US012799541B2

(12) United States Patent
Youngbull et al.

(10) Patent No.: US 12,799,541 B2
(45) Date of Patent: Nov. 17, 2026

(54) APPARATUS AND METHOD FOR QUANTIFYING ENVIRONMENTAL DNA WITH NO SAMPLE PREPARATION

(71) Applicant: University of Montana, Missoula, MT (US)

(72) Inventors: Aaron Cody Youngbull, Polson, MT (US); James Joseph Elser, Polson, MT (US)

(73) Assignee: University of Montana, Missoula, MT (US)

( * ) Notice: Subject to any disclaimer, the term of this patent is extended or adjusted under 35 U.S.C. 154(b) by 649 days.

(21) Appl. No.: 18/267,595

(22) PCT Filed: Dec. 16, 2021

(86) PCT No.: PCT/US2021/063927
§ 371 (c)(1),
(2) Date: Jun. 15, 2023

(87) PCT Pub. No.: WO2022/133152
PCT Pub. Date: Jun. 23, 2022

(65) Prior Publication Data

US 2024/0052431 A1 Feb. 15, 2024

Related U.S. Application Data

(60) Provisional application No. 63/126,784, filed on Dec. 17, 2020.

(51) Int. Cl.
*C12Q 1/6888* (2018.01)
*C12Q 1/6851* (2018.01)
(Continued)

(52) U.S. Cl.
CPC ......... *C12Q 1/6888* (2013.01); *C12Q 1/6851* (2013.01); *G01N 1/34* (2013.01);
(Continued)

(58) Field of Classification Search
CPC .... C12Q 1/6888; C12Q 1/6851; C12Q 1/686; G01N 1/34; G01N 35/08;
(Continued)

(56) References Cited

U.S. PATENT DOCUMENTS

2011/0086352 A1 4/2011 Bashir et al.
2011/0092376 A1 4/2011 Colston, Jr. et al.

FOREIGN PATENT DOCUMENTS

WO 2014145555 A1 9/2014
WO 2015200717 A2 12/2015
(Continued)

OTHER PUBLICATIONS

Eicher D. and Merten C. A., “Microfluidic devices for diagnostic applications,” Expert Review of Molecular Diagnostics 11(5):505-519, 2011.
(Continued)

*Primary Examiner* — Cynthia B Wilder
(74) *Attorney, Agent, or Firm* — Glenn H. Lenzen; Elevated IP, LLC

(57) ABSTRACT

A fieldable processing and detection apparatus for automatically collecting, preparing, Identifying and quantifying environmental DNA in samples of a material of Interest. Environmental samples of materials of interest are combined with polymerase chain reaction (PGR) reagents that are selectively compatible with the material of Interest and mixed. Various processing methods may be employed at the discretion of the operator and include droplet concentration, thermoprofiling, particle separation and other techniques or methods that are compatible with and suitable for the specific material of interest and the testing environment The system will selectively lyse cells, breaking down the cell membrane via mechanical disruption, ultrasound, thermocycling, or other suitable techniques and thereafter quantify
(Continued)

the preamplified concentration of target nucleic add sequences using digital quantification.

11 Claims, 3 Drawing Sheets

(51) Int. Cl.
*G01N 1/34* (2006.01)
*G01N 35/00* (2006.01)
*G01N 35/08* (2006.01)

(52) U.S. Cl.
CPC ... *G01N 35/08* (2013.01); *G01N 2035/00366* (2013.01); *G01N 2035/00475* (2013.01); *G01N 2035/00534* (2013.01)

(58) Field of Classification Search
CPC .......... G01N 2035/00366; G01N 2035/00475; G01N 2035/00534; G01N 2035/00465; G01N 1/02; B01F 25/1051; B01F 33/305; C12N 15/1003
See application file for complete search history.

(56) References Cited

FOREIGN PATENT DOCUMENTS

| | | | | |
|---|---|---|---|---|
| WO | 2016064755 | A2 | 4/2016 | |
| WO | WO-2018098438 | A1 * | 5/2018 | ........... C12Q 1/6848 |

OTHER PUBLICATIONS

Fair R. B., "Digital microfluidics: is a true lab-on-a-chip possible?", Microfluid Nanofluid 3:245-281, 2007.
Ray T., "Low power, high throughput continuous flow PCR instruments for environmental applications," Dissertation, Arizona State University, Dec. 2013, 181 pages.

* cited by examiner

APPARATUS AND METHOD FOR QUANTIFYING ENVIRONMENTAL DNA WITH NO SAMPLE PREPARATION

CROSS-REFERENCE TO RELATED APPLICATIONS

This application is a 371 national stage application of international application No. PCT/US2021/063927, filed Dec. 16, 2021, which claims priority to U.S. Provisional Patent Application No. 63/126,784 filed on Dec. 17, 2020, each of which is incorporated herein by reference in its entirety.

FIELD OF THE INVENTION

The present invention relates to an apparatus and method for on-site detection of nucleic acids without handling and physical/chemical extraction by a human operator. More specifically, the present invention relates to an apparatus and method for automatically collecting test samples of a material of interest measured continuously at arbitrary intervals and analyzed for environmental DNA or RNA (both collectively referred to herein as "eDNA") without the need to manually collect, concentrate, breakdown, and extract materials to obtain target eDNA in the sample collection volume.

BACKGROUND OF THE INVENTION

Environmental DNA or eDNA is DNA that is collected from a variety of environmental samples such as surfaces, soil, seawater, snow, or even air as opposed to being obtained directly from an individual organism. The analysis of eDNA collected from environmental samples is especially useful in detecting the presence of target species, especially those that are rare in the environment (such as newly invasive species or species of conservation concern). The method can also be used to quantify organism abundance. Organism abundance is measured in plant or animal counts, while eDNA concentration is measured in gene copy numbers. Relating total organism abundance in any environment to eDNA concentrations in a small sample of that environment is one of the many reasons for studying eDNA. Information about an entire population may be derived from a small sample taken from the environment in which the population resides or into which it sheds DNA. However, making the leap from measuring extant nucleic acids to inferring information about organism presence/absence, abundance, behavior, and health presents many challenges.

For example, eDNA introduction rates, fluid flow patterns, sunlight- and temperature-induced degradation, background chemicals, and microbial consumers in the local sample are all known to strongly affect the distribution and stable lifetime of eDNA. If eDNA is present at the time of sample collection, collection techniques, processing methodologies, and processing time delays will also strongly affect quantification of gene copy numbers. Accordingly, minimizing the number of sample collection and processing steps permits significant simplification of sample collection and processing instrumentation and enhances quantification accuracy by avoiding losses and variations in efficiencies that confound detection of eDNA targets and precise quantification of their gene copy number.

Environmental DNA comes in two different forms: standard-eDNA, which involves nucleic acids contained within live or dead cells or viruses, and cell-free eDNA, which involves target nucleic acids that are free in solution or bound with acellular particles dispersed in the environmental sample. Little is known about cell-free eDNA levels as compared to standard-eDNA levels in the environment and the relationship of cell-free eDNA levels to organism abundance. First, the environmental decay rates of cell-free eDNA are unknown but are likely much faster than the decay rates of standard-eDNA. Both are influenced by many environmental factors. Secondly, cell-free eDNA stabilization methods that are compatible with downstream analysis of laboratory returned samples are far more challenging than standard-eDNA stabilization methods. Accordingly, quantification of cell-free eDNA is extremely difficult if the environmental sample is not analyzed directly in the field at the time of collection.

In contrast, standard-eDNA, being protected by cell membranes or walls, decays over a longer period and can be stabilized for shipment using a variety of readily available reagents. The stabilizing reagents are easily removed by passing them through a filter as the cells which contain the standard-eDNA are collected and processed at the shipping destination. Moreover, standard-eDNA is more commonly studied because concentrated target eDNA facilitates detection of trace levels of the target of interest. Concentrating standard-eDNA is accomplished by simply collecting cells from a large sample volume onto a filter having a pore size that is larger than the non-cell associated molecules, debris, and background matrix of the sample fluid. The fluid that passes through the filter in the standard-eDNA detection method (the filtrate) is commonly discarded, yet it carries a host of molecules, including the cell-free eDNA molecules that would otherwise be discarded using standard analysis methods. These cell-free eDNA molecules may include DNA from target species, and the concentrations thereof in the filtrate are also likely to be present in proportion to target organism abundance.

Prior art methodologies attempt to identify the presence of ubiquitous bacteria in test specimens via determination of bacterial load by applying real-time polymerase chain reaction ("PCR") techniques using a broad range (universal) probe and a set of primers. See Nadkami, M. A., F. E. Martin, N. A. Jacques, and N. Hunter, *Determination of Bacterial Load by Real-Time PCR Using a Broad Range (Universal) Probe and Primers Set.* 2002. Microbiology 148:257-266) without any sample preparation. The idea therein presented is that the target microbes would naturally lyse or undergo lysis, which is a breaking down of the cell membrane, and thereby release their DNA content during exposure to a 10-minute heating period that is naturally part of the internal quantification process of the instrument disclosed herein. Quantification of genes by this method would normally not work in a standard quantitative PCR (qPCR) instrument, as the complex sample contents and background proteins and molecules released by cells upon heating would disrupt the quantification. Quantification in standard real-time qPCR is typically based on comparing reaction rates to a control sample of known concentration, and accuracy and reliability may be compromised by potential interfering molecules and other factors, as noted above.

In view of the foregoing, it will be apparent to those skilled in the art from this disclosure that a need exists for fieldable eDNA collection and detection apparatus and methods that overcome the obstacles presented by the size and stabilization issues surrounding the analysis of cell-free eDNA. The present invention addresses these needs in the art as well as other needs, all of which will become apparent to those skilled in the art from the accompanying disclosure.

SUMMARY OF THE INVENTION

In one aspect, the present invention discloses a fieldable processing and detection apparatus for automatically collecting, sampling, preparing, and quantifying eDNA in samples of a material of interest measured continuously or at arbitrary intervals.

In another aspect, the apparatus of the present invention quantifies eDNA in samples of a material of interest in the field without the use of hardware consumables.

In still another aspect, the apparatus of the present invention includes a device for storing reagents that are combined with the collected sample to enable downstream sample analysis.

In yet another aspect, the apparatus of the present invention includes a sample inlet and a device for storing reagents used to clean the sample inlet.

In an aspect of the present invention, a fieldable detection apparatus measures eDNA in collected sample volumes without dissociating the target eDNA in the sample volumes from cells or other background molecules contained within a collected sample volume.

In another aspect of the present invention, a field detection apparatus measures the levels of cell-free eDNA in a molecule of interest before decay thereof and without the use of stabilization methods.

In yet another aspect of the present invention, robust cell-free eDNA detection technologies are disclosed which detect and measure accurately cell-free eDNA levels in the presence of cross-sensitivity and inhibitory reactions typical of actual environmental samples.

BRIEF DESCRIPTION OF THE DRAWINGS

Referring now to the attached drawings which form a part of this original disclosure.

DETAILED DESCRIPTION OF THE PREFERRED EMBODIMENTS

Selected embodiments of the present invention will now be explained with reference to the drawings. It will be apparent to those skilled in the art from this disclosure that the following descriptions of the embodiments of the apparatus and method herein disclosed are provided for illustration purposes only and not to limit the invention as defined by the accompanying drawings and specification.

Figure 1:
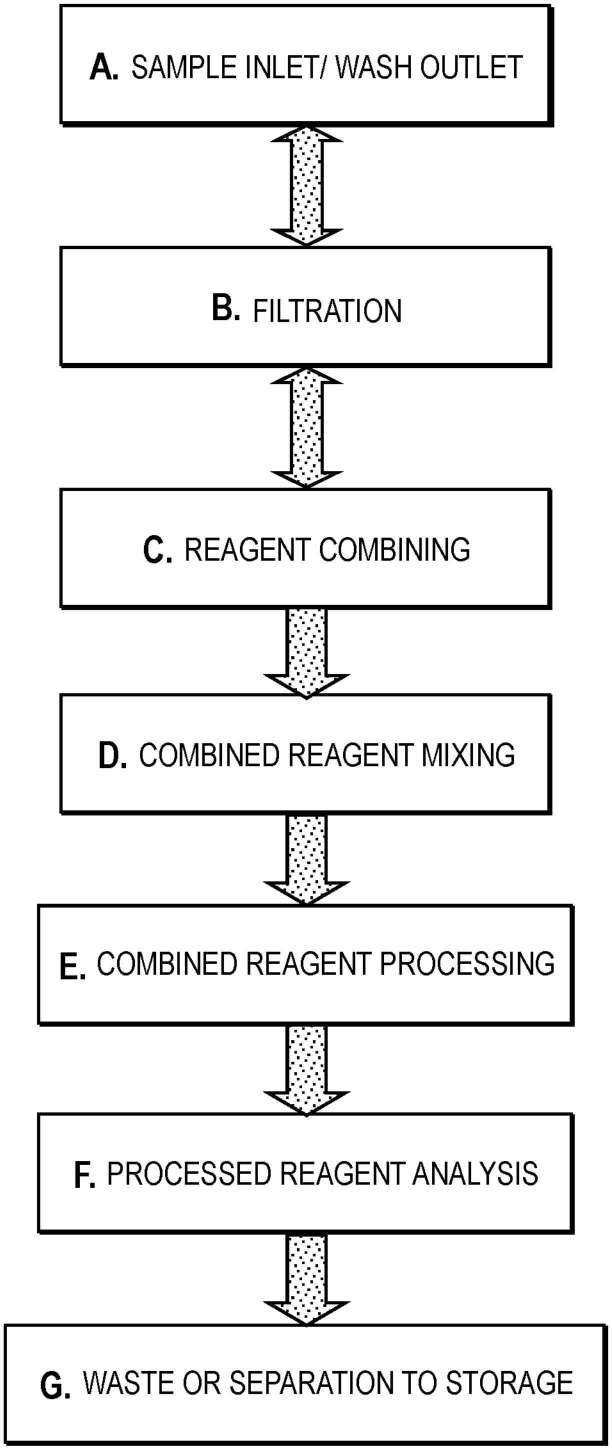
FIG. 1 is a flow diagram of a method for collecting and quantifying environmental DNA in the field.
Figure 3:
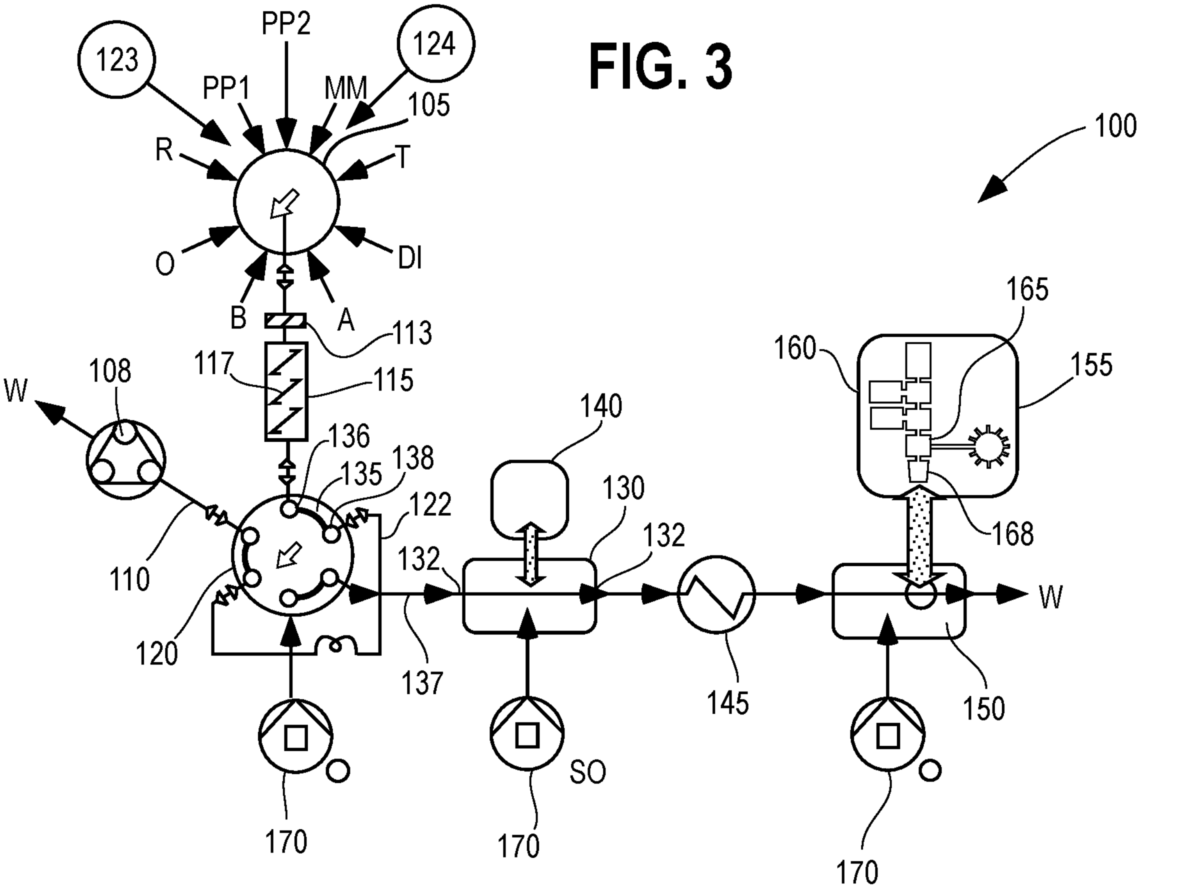
FIG. 3 is a schematic diagram of a fully automated system for the collection and quantification of environmental DNA in the field in accordance with the present invention.

Referring to FIG. 1, a flow chart presents the steps of the method of collecting and quantifying environmental DNA ("eDNA") in the field in accordance with an embodiment of the present invention. The apparatus hereinbelow described in greater detail is transported to the field location of the material to be sampled. By way of example and not of limitation, the material of interest may be a body of water such as a lake, stream, or reservoir, or solid material such as soil, plant matter or biological material. At step A, a collected sample of the material of interest is introduced into the system via a sample inlet and filtered (step B). It may be selectively washed or rinsed before further processing, and the wash is discharged via a wash outlet W, as shown in the embodiment of FIG. 3. At step C, a mixing valve combines at least one of a plurality of selected reagents that are compatible with the material of interest. The selected reagents may be added individually to the sample directly from a container in which the reagent is shipped by its manufacturer or may be stored in a reagent storage bank portion of the system for adding to the sample. In either case, the reagents and the sample are then mixed at step D, thereby forming a mixture thereof. Exemplary reagents may include but are not limited to air, a gas, bleach, water, primer/probe sets. Master Mix (commercially available batch mixtures of PCR reagents at preselected concentrations chosen for the specific task at hand, such a PCR master mix produced by Millipore Sigma), reverse transcriptase, digestion enzymes, fluorinated oil, and the like. The mixed combined reagents and sample of the material of interest are then processed at step E. Various processing methods may be employed at the discretion of the operator and include droplet concentration, thermoprofiling, particle separation and other techniques or methods that are compatible with and suitable for the specific material of interest and the testing environment. Analysis of the processed reagents is performed at step F and may be performed by such exemplary analysis methods as fluorescence emission detection, absorption spectroscopy, video analysis and/or polarization anisotropy detection. At step G, the processed sample of the material of interest is isolated and separated from the mixture for storage, and any waste material is discarded.

Figure 2:
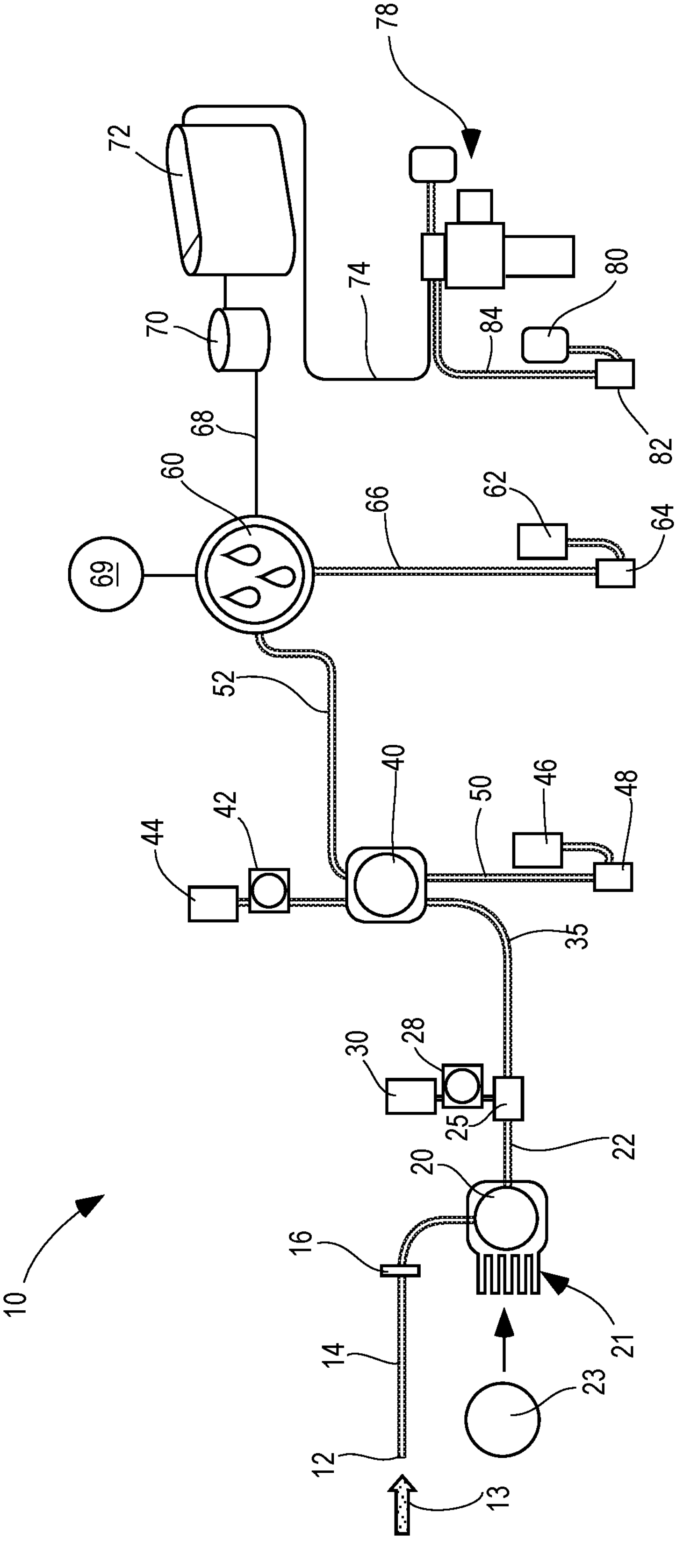
FIG. 2 is a schematic diagram of a system for the collection and quantification of environmental DNA in the field in accordance with the present invention.

FIG. 2 illustrates the elements of an apparatus for the collection, measurement, and quantification of environmental DNA in target eDNA that may be present in a sample of interest is shown generally at 10. The apparatus includes an environmental sample inlet 12 adapted to collect an environmental sample 13 from the sample of interest and to transmit it via conduit or tubing 14 operatively connected thereto and in fluid communication therewith via a front-end filter 16 to a mixing valve 20. By way of example and not of limitation, the front-end filter may be a germicidal filter having a pore size of 200 nm. However, it is to be understood that filters having other pore sizes may also be used without departing from the scope of the present invention. The mixing valve is adapted to selectively introduce at least one of a plurality of reagents selectively compatible with the material of interest as noted above. By way of example and not of limitation, selective reagents may include primer probes, mixer materials of preselected compositions, bleach, distilled water, air, and other materials as needed. The reagents are introduced to the system via one or more of a plurality of input ports 21 in fluid communication with the mixing valve and with a reagent storage bank portion 23 of the system for any given sampling procedure. Output from the mixing valve is communicated via conduit 22 to a three-way valve 25 that is operatively connected to a first peristaltic pump 28 and a first fluid reservoir 30.

The environmental sample 13 is transferred via conduit 35 to a sample injection apparatus or injector 40. The sample injection apparatus is connected to a second peristaltic pump 42 and a second fluid reservoir 44 and to an enhanced fluorinated oil reservoir 46 via pump or valve 48 and conduit 50. The first and second fluid reservoirs 30 and 44 each contain polymerase chain reaction (PCR) reagents and the environmental sample. The sample injector combines oil from the reservoir 46 with material from reservoir 44 to form a sample for testing purposes which is then communicated via conduit 52 to a digital droplet generator or instrument 60. The droplet generator mixes the testing sample with a droplet generation oil held in reservoir 62 which is communicated to the droplet generator by pump or valve 64 via conduit 66. The oils contained in reservoirs 46 and 62 are automatically mixed with the environmental sample and PCR reagents by an automated control system 69 of the digital droplet instrument. The droplets are then communicated via tubing or conduit 68 to a heater 70 and a thermocycler 72 (an instrument used to amplify DNA and RNA samples by the polymerase chain reaction) and then via conduit or tubing 74 to a separation and detection apparatus or detector 78. Reservoir 80 holds separation oil used in the detection process that is delivered to the detector via valve or pump 82 and conduit 84 operatively connected thereto intermediate the reservoir 80 and the separation and detection apparatus 78.

Referring now to FIG. 3, a fully automated apparatus or instrument for the collection and quantification of eDNA from environmental samples is shown generally at 100 in accordance with an embodiment. As will be described in greater detail below with respect to each component of the apparatus, as an overview, the apparatus uses emulsion droplet polymerase chain reaction (PCR) methodologies to amplify the concentration of target nucleic acid sequences associated with biological materials below a certain size limit (to avoid clogging) in aqueous samples. The nucleic acid sequences themselves are typically physically associated with biological cells or cellular debris, particles, or suspended freely within the aqueous sample. Depending upon the material, the instrument may selectively lyse cells, which is breaking down the cell membrane via mechanical disruption, ultrasound, thermocycling, or other suitable techniques known in the art and thereafter quantifying the preamplified concentration of target nucleic acid sequences using digital quantification. With the proper selection of reagents and design of the thermocycling profile, the instrument can perform different reactions, including PCR or reverse transcription PCR (RT-PCR). The instrument uses a fluorescence flow cell detector to excite and measure the fluorescence emission of passing emulsion droplets.

A selector valve 105 serves as the instrument input point and includes a plurality of inlets for inserting primer probe targets or environmental samples of a material of interest shown by way of illustration and not of limitation at PP1 and PP2. The samples along with selected reagents R. Master Mix MM, oil O, bleach B, air A, digestion enzymes DI and heat T are inserted into the system via respective input ports having corresponding alphabetic identifiers formed in the selector valve, as indicated in FIG. 3. Inputs are arbitrary, and a larger number of input ports than shown for illustrative purposes allow for more reagents to be introduced into the reaction as may be required for a material of interest.

A pump 108 operatively connected to the system via conduit 110 pulls and pushes reagents from the selector valve, through a front filter 113 and a mixing zone 115, and through a reaction injector valve 120 and a fixed volume sample injection loop 122. Pump 108 is shown as a peristaltic pump; however, it is to be understood that pumps of other configurations and operation may also be used without departing from the scope of the present invention. The pump also pushes waste material to a suitable waste collection point W and pushes reagents R back through the selector valve during cleaning procedures.

After cleaning and before a next environmental sample template is injected, the valve and the downstream loop is primed with an oil, designated as "O" in FIG. 3, a fluorinated oil such as 3M™ Novec™ 7500 Engineered Fluid, Sigma-Aldrich's Fluorinert™ FC-40 and the like. The selector valve connects upstream to a reagent storage area 123 which is accomplished via standard plastic Luer-lock syringes for each reagent. The syringes are individually filled and replaced by the operator whenever they run out. Reagents may also be supplied from a reagent bank 124.

In field operation of the analytical apparatus of the present invention, it is important to exclude debris and foreign matter which may be present in an environmental sample to prevent clogging of the system components. Accordingly, a front filter 113 is adapted to filter any debris larger than the smallest constriction in the instrument. In the embodiment of FIG. 3, the point of smallest constriction is a 100-micron constriction inside a microfluidic droplet generator chip 130. However, it is to be understood that other system configurations may require filters of different sizes, without departing from the scope hereof. Preferably, the filter is replaced after every single run. Alternatively, the filter can also be cleaned by backflushing from a reagent bank during a cleaning cycle to extend filter's lifetime.

The environmental samples and the reagents are combined in mixing zone 115 before injecting them downstream to the microfluidic droplet generator chip 130. In the embodiment shown, the mixing zone is in the form of circuitous segment of fluoropolymer tubing 117 having exemplary dimensions of 1/16" OD×0.03" ID. However, other tubing sizes and configurations may be employed. The aqueous reagents are sequentially pulled into this zone via pump 108 to constitute the reaction. Typical total reaction volumes are 25-microliters each and are composed of at a minimum PP, T, MM, and DI. A long path with a relatively large internal diameter mixing zone is desired to achieve non-laminar flow and optimum mixing efficiency of the reaction components.

The reaction injector valve 120 further includes a two-position valve, also referred to herein as an injector 135 in fluid communication with the mixing zone at a first end 136 thereof and in fluid communication at a second end 138 thereof with the fixed volume sample injection loop 122. The injector 135 is adapted to fill the fixed volume sample injection loop 122. The fixed volume sample injection loop includes a representative 25-microliter reaction volume and is adapted to inject a continuously flowing stream via conduit 137 into the microfluidic droplet generator chip 130. Other embodiments of the instrument can use multiple loop injectors to allow for different reaction volumes. For example, a two-loop injector having eight ports instead of six ports as shown in the embodiment of FIG. 3 allows for the selector to fill one injection loop while the other injection loop is being pushed through the microfluidic droplet generator chip 130. In this configuration, two different reaction volumes may be processed concomitantly, and cleaning cycles can be done in parallel to reaction injections.

The reaction among the combined reagents and the environmental sample completed via the addition of a selected amount of surfactinated oil (SO) in the microfluidic droplet generator chip 130. In an embodiment, a side-on connection chip having side connections 132 is used to optimize smooth droplet flow. Fluid port connections which come in at 90 degrees to the surface of the microfluidic chip can cause undesirable droplet breakup. A camera 140 films macro imaging droplet formation during the process thereby providing real-time practical feedback of the fluid flow rates and the reaction to the instrument operator.

A multi zone thermocycler 145 controls the temperatures at various stages or zones during the reaction. For standard PCR reactions which use hydrolysis probes and hot start polymerase, exemplary zone temperatures are 95 ° C, 60 ° C, and 95 ° C For RT-PCR reactions, the injected reagents would additionally include reverse transcriptase, an enzyme that is used to generate complimentary DNA from an RNA template, and the number of zones and zone temperatures may be modified accordingly. The dimensions of the thermocycler are driven primarily by the flow rates through the droplet generator chip and the tubing internal diameter. Closed-loop temperature control is achieved from temperature sensor feedback. No active cooling is used in this embodiment. Accordingly, airflow and proper insulation is critical.

The droplets are then transferred to a droplet separator chip 150, a microfluidic chip operatively connected to a fluorescence flow cell detector 155. The microfluidic chip is adapted to introduce additional O oil to separate and to image the light emanating from passing droplets. The fluorescence flow cell detector includes a multi-color epi-fluorescence confocal system 160. The system can use LEDs or lasers to excite passing emulsion droplets. A plurality of confocal apertures 165 on the back focal plane of each fluorescence light path ensure no out-of-focus light arrives at the detector. High-speed, high-sensitivity, and one or more low-noise detectors 168 are used to collect emission light from passing droplets. The fluorescence flow cell detector 155 is held in fixed alignment with the droplet separator chip.

One or more non-pulsatile displacement pumps 170 that can drive and control specimen volumes over a broad range extending from sub-microliter per minute flows necessary for droplet generation, separation, and flow to hundreds of microliters per minute necessary for refill. Three-way valves connecting the positive displacement pumps to oil storage reservoirs would be necessary for long deployment times (not shown).

In trials performed with the apparatus of the present invention, digital droplet PCR samples were tested using presence/absence statistics on large numbers of nanoliter PCR reactions to quantify gene copy numbers. Accordingly, the process herein disclosed does not depend on reaction rate and thus (unlike other technologies) is not compromised by potential interfering molecules or other factors. The apparatus and associated methodology disclosed herein achieves gene quantification of the raw environmental sample with no sample preparation.

Subsequent tests involved running environmental water samples through a much smaller filter that would not allow the passage of cells. Such a small filter (200 nm pore size) is often referred to as a ‘germicidal’ filter. Gene detection nonetheless was achieved, thereby indicating that cell-free eDNA was present in the sample and that it, along with standard-eDNA associated with cells, may be quantified automatically with simplification to the sample collection and processing stages. Thus, the automated front end mixer sample injection loop in conjunction with the digital droplet PCR instrument (DNA-Tracker) enables automated collection of environmental water and automated introduction of PCR reagents, replacing the need to combine reagents prior to introducing samples into the device.

Connected with a single tubing connection, the automated front-end mixer and the DNA-Tracker becomes fully automated and represents what may properly be called the world's first “DNA Smoke Alarm”, capable of collecting raw samples every few minutes and quantifying gene copy numbers in the sample with no human intervention. The automated DNA-Tracker contains all necessary reagents stored internally, requires no hardware consumables, and has no moving parts other than pumps and valves.

While only selected embodiments have been chosen to illustrate the present invention, it will be apparent to those skilled in the art from this disclosure that various changes and modifications can be made herein without departing from the scope of the invention as defined herein. Furthermore, the foregoing descriptions of the embodiments according to the present invention are provided for illustration only, and not for limiting the invention as defined by the appended claim and its equivalents.

What is claimed is:

1. An apparatus for collecting, measuring, and quantifying environmental DNA in target eDNA in an environmental sample of a material of interest in the field, the apparatus comprising:

an environmental sample inlet;

a mixing valve in fluid communication with the environmental sample inlet;

a filter disposed intermediate the environmental sample inlet and the mixing valve;

a plurality of polymerase chain reaction (PCR) reagents that are compatible with the material of interest;

a plurality of input ports in fluid communication with the mixing valve, each of the plurality of input ports being adapted to introduce at least one of the plurality of PCR reagents to the mixing valve;

a three-way valve in fluid communication with the mixing valve and adapted to receive output therefrom and to communicate the mixing valve output to a first peristaltic pump, a first fluid reservoir, and a sample injection apparatus or injector;

a second peristaltic pump in fluid communication with the first peristaltic pump, a second fluid reservoir and with the sample injecting apparatus or injector, the second peristaltic pump, the second fluid reservoir and the sample injecting apparatus each being adapted to receive output from the mixing valve;

a third reservoir in fluid communication via a valve or pump with the sample injection apparatus, the third reservoir being adapted to receive and store a first oil;

a fourth reservoir adapted to receive and store a second oil;

a droplet generator in fluid communication with the sample injection apparatus or injector and with the fourth reservoir via a pump or valve, the droplet generator being adapted to mix the environmental sample, PCR reagents, the first and second oils and to form one or more droplets thereof;

a heater in fluid communication with the droplet generator and adapted to receive one or more droplets of the mixed environmental sample, PCR reagents, and the first and second oils;

a thermocycler operatively connected to the heater, the thermocycler being adapted to amplify eDNA samples in each of the one or more droplets via a PCR;

a separation and detection apparatus or detector in fluid communication with the thermocycler, the detector being adapted to receive one or more droplets of the mixed environmental sample, PCR reagents, and first and second oils from the thermocycler and to detect eDNA therein contained; and a fifth reservoir adapted to hold a third oil adapted for use in the detection of eDNA, the fifth reservoir being in fluid communication with the separation and detection apparatus or detector via a valve or pump which is operatively connected thereto intermediate the reservoir and the separation and detection apparatus.

2. The apparatus of claim 1 wherein plurality of polymerase chain reaction (PCR) reagents include primer probes, mixer materials of preselected compositions, bleach, distilled water, air, or mixtures thereof.

3. The apparatus of claim 1 wherein the first oil comprises an enhanced fluorinated oil.

4. The apparatus of claim 1 wherein the second oil comprises a droplet generation oil.

5. The apparatus of claim 1 wherein the third oil comprises a separation oil.

6. A fully automated system for collecting, measuring, and quantifying environmental DNA in target eDNA in an environmental sample of a material of interest in the field, the system comprising:

a selector valve having a plurality of input ports or inlets, each of the plurality of input ports being adapted to selectively receive an environmental sample of a material of interest or one of a plurality of polymerase chain reaction (PCR) reagents that are compatible with the material of interest;

a reagent storage area in fluid communication with the plurality of input ports or inlets in the selector valve;

a filter adapted to filter out debris and foreign matter in an environmental sample of a material of interest;

a mixing zone in fluid communication with the selector valve via the filter, the mixing zone being adapted to combine the environmental sample of a material of interest and at least one of the plurality of PCR reagents that are compatible with the material of interest;

a pump operatively connected to the system, the pump being adapted to urge the environmental sample and selected PCR reagents from the selector valve through the filter and mixing zone;

a reaction injector valve adapted to receive the environmental sample and selected PCR reagents from the mixing zone in response to forces generated by the pump, the reaction injector valve including a two position valve or injector in fluid communication with the mixing zone at a first end thereof and with a fixed volume sample injection loop at a second end thereof;

a microfluidic droplet generator chip in fluid communication with the reaction injector valve and in fluid communication with a multi-zone thermocycler;

a camera adapted to film macro imaging droplet formation during the process, thereby providing real-time practical feedback of the fluid flow rates and the reaction between the environmental sample and the selected PCR reagents;

a microfluidic droplet separator chip in fluid communication with the microfluidic droplet generator chip, the microfluidic droplet separator chip including a fluorescence flow cell detector adapted to separate and create images of light emanating from passing droplets; and one or more displacement pumps adapted to drive and control the flow rate of specimen volumes.

7. The system of claim 6 wherein the microfluidic droplet generator chip is adapted to introduce a selected amount of surfactinated oil (SO) to the combined reagents and the environmental sample, whereby the reaction among the combined reagents and the environmental sample is completed.

8. The system of claim 6 wherein the microfluidic droplet generator chip comprises a side-on connection chip having opposed side connections, the side-on connection chip being adapted to optimize smooth droplet flow.

9. The system of claim 6 wherein the fixed volume sample injection loop includes a preselected volume adapted to inject a continuously flowing stream of the combined reagents and environmental sample into the microfluidic droplet generator chip.

10. The system of claim 6 wherein the microfluidic droplet generator chip includes two or more fixed volume sample injection loops, each having a different reaction volume.

11. The system of claim 6 wherein the microfluidic droplet separator chip is adapted to introduce additional oil to the flow of droplets of combined reagents and the environmental sample to separate and to image the light emanating from passing droplets.

* * * * *